(12) United States Patent
Wheeler et al.

(10) Patent No.: US 7,173,123 B2
(45) Date of Patent: *Feb. 6, 2007

(54) METHODS FOR DETECTION OF CHLORAL HYDRATE IN DICHLOROACETIC ACID

(75) Inventors: Patrick Wheeler, Carlsbad, CA (US); Daniel C. Capaldi, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 10/679,805

(22) Filed: Oct. 6, 2003

(65) Prior Publication Data

US 2005/0113569 A1 May 26, 2005

Related U.S. Application Data

(63) Continuation of application No. 10/059,776, filed on Jan. 29, 2002, now Pat. No. 6,645,716.

(60) Provisional application No. 60/264,920, filed on Jan. 30, 2001.

(51) Int. Cl.
   *C07H 21/00* (2006.01)
   *C07H 21/02* (2006.01)
   *C07H 21/04* (2006.01)
   *C12Q 1/68* (2006.01)

(52) U.S. Cl. .................. 536/25.3; 536/23.1; 435/6

(58) Field of Classification Search .............. 435/6; 536/23.1, 25.3

See application file for complete search history.

(56) References Cited

U.S. PATENT DOCUMENTS

| 5,292,928 | A | 3/1994 | Miltenberger | 560/226 |
| 5,959,099 | A | 9/1999 | Cheruvallath et al. | 536/26.1 |
| 6,005,094 | A | 12/1999 | Simon et al. | 536/24.5 |
| 6,645,716 | B2 * | 11/2003 | Wheeler et al. | 435/5 |

FOREIGN PATENT DOCUMENTS

| DE | 610 317 | 3/1935 |
| DE | 852 997 | 10/1952 |

OTHER PUBLICATIONS

Atkinson et al. Solid phase synthesis of oligodeoxynucleotides by the phosphite-triester method. Chapter 3 pp. 35-81, in Oligonucleotide Synthesis— A Practical Approach, MJ Gait Editor, IRL press, 1984.*
Morrison et al. Organic Chemistry Second Edition, Allyn and Bacon, Inc. Boston 1966, pp. 428-429.*
Beaucage, S. L. et al., "Advances in the Synthesis of Oligonucleotides by the Phosphoramidite Approach," *Tetrahedron*, 1992, 48, 2223-2311.
The Supplementary European Search Report dated Apr. 20, 2004 (EP 02 70 6042).
Falbe, J., et al., "Römpp kompakt basislexikon chemie," *Georg Thieme Verlag, Stuttgart*, 1998, 401 and 531.
Korte, F., et al., "Notiz zur synthese des xanthopterins," *Chem. Ber.*, 1953, 86, 114-116.
U.S. Appl. No. 10/403,692, Isis Pharmaceuticals, Inc.

* cited by examiner

*Primary Examiner*—Jezia Riley
(74) *Attorney, Agent, or Firm*—Isis Patent Department

(57) ABSTRACT

Methods for detecting chloral hydrate in dichloroacetic acid are described.

9 Claims, No Drawings

METHODS FOR DETECTION OF CHLORAL HYDRATE IN DICHLOROACETIC ACID

RELATED APPLICATIONS

This application is a continuation of Ser. No. 10/059,776 filed Jan. 29, 2002, now U.S. Pat. 6,645,716, which claims benefit to Ser. No. 60/264,920 filed Jan. 30, 2001. The contents of each of the foregoing U.S. Patent applications are incorporated herein by reference in their entirety.

FIELD OF THE INVENTION

This invention relates generally to novel methods for detecting chloral hydrate in dichoroacetic acid.

BACKGROUND OF THE INVENTION

It is well known that most of the bodily states in multi-cellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are undergoing clinic trials for such uses. Oligonucleotides can also serve as competitive inhibitors of transcription factors, which interact with double-stranded DNA during regulation of transcription, to modulate their action. Several recent reports describe such interactions (see, for example, Bielinska, A., et. al., *Science,* 250 (1990), 997–1000; and Wu, H., et. al., *Gene,* 89, (1990), 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual,* Second Ed., J. Sambrook, et al., Eds., Cold Spring Harbor Laboratory Press, 1989; and *Current Protocols In Molecular Biology,* F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual,* supra. See also "DNA-protein interactions and The Polymerase Chain Reaction" in Vol. 2 of *Current Protocols In Molecular Biology,* supra. Oligonucleotides and their analogs have also been developed and used in molecular biology in a variety of procedures as probes, primers, linkers, adapters, and gene fragments.

The widespread use of such oligonucleotides has increased the demand for rapid, inexpensive and efficient procedures for their modification and synthesis. Early synthetic approaches to oligonucleotide synthesis included phosphodiester and phosphotriester chemistries. Khorana et al., *J. Molec. Biol.* 72 (1972), 209; Reese, *Tetrahedron Lett.* 34 (1978), 3143–3179. These approaches eventually gave way to more efficient modern methods, such as the use of the popular phosphoramidite technique (see, e.g., *Advances in the Synthesis of Oligonucleotides by the Phosphoramidite Approach,* Beaucage, S. L.; Iyer, R. P., *Tetrahedron,* 48 (1992) 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

Solid phase techniques continue to play a large role in oligonucleotide synthetic approaches. Typically, the 3'-most nucleoside is anchored to a solid support which is functionalized with hydroxyl or amino residues. The additional nucleosides are subsequently added in a step-wise fashion to form the desired linkages between the 3'-functional group of the incoming nucleoside and the 5'-hydroxyl group of the support bound nucleoside. Implicit to this step-wise assembly is use of a protecting group to render unreactive the 5'-hydroxy group of the incoming nucleoside. Following coupling, the 5'-hydroxy group is removed through the judicious choice of a deprotecting reagent.

Dichloroacetic acid (DCA) is a commonly used reagent for deblocking nucleotides during oligonucleotide synthesis. Because the addition of new nucleosides involves the repeated use of dichloroacetic acid for deprotecting the 5'-hydroxy group, it is important that this reagent be as free as possible of contaminants which may propagate impurities and produce improper sequences of the target oligonucleotide. Accordingly, methods are needed for detecting such impurities in dichloroacetic acid. The present invention is directed to these, as well as other, important ends.

SUMMARY OF THE INVENTION

It has been discovered that chloral hydrate is a common contaminant in commercially prepared dichloroacetic acid. It has been further discovered that chloral hydrate reacts with the 5'-hydroxy group of nucleosides during the course of oligonucleotide synthesis to form undesired side-products that are removed, if at all, only with great difficulty. It has been further discovered that chloral hydrate in dichloroacetic acid can be detected and its concentration accurately measured, by comparing the integral of a nuclear magnetic resonance peak of the CH proton of chloral hydrate with a known amount of internal standard.

Accordingly, it is an object of the present invention to provide methods for detecting chloral hydrate in dichloroacetic acid.

It is a further object of the present invention to provide methods for measuring the concentration of chloral hydrate in dichloroacetic acid, particularly, for detecting chloral hydrate and measuring its concentration in dichloroacetic acid which is to be used as a deprotecting reagent in oligonucleotide synthesis.

It is a further object of the present invention to provide methods for preparing oligonucleotides that are free of the impurity which is caused by chloral hydrate present in dichloroacetic acid.

These, as well as other important objects, will be become apparent during the following detailed description.

DETAILED DESCRIPTION OF THE INVENTION

In a first embodiment, the present invention provides an analytical method comprising determining whether or not a nuclear magnetic resonance spectrum taken from a sample of dichloroacetic acid includes a nuclear magnetic resonance peak associated with a CH proton of chloral hydrate. In certain preferred embodiments, the method further comprises comparing an integral of said nuclear magnetic resonance peak associated with said CH proton of chloral hydrate with an integral of a nuclear magnetic resonance peak associated with at least one proton of said dichloroacetic acid. In certain preferred embodiments, the method further comprises calculating a concentration of chloral hydrate in said dichloroacetic acid based upon said comparison of integrals of nuclear magnetic resonance peaks. In certain preferred embodiments, the calculated concentration of chloral hydrate is less than 15 ppm. In certain preferred embodiments, the calculated concentration of chloral hydrate is less than 10 ppm. In certain preferred embodiments, the calculated concentration of chloral hydrate is less than 1 ppm.

In another embodiment, the present invention provides an analytical method comprising determining whether or not a nuclear magnetic resonance spectrum taken from a sample of dichloroacetic acid includes a nuclear magnetic resonance peak associated with a CH proton of chloral hydrate, further comprising:

adding at least one organic solvent to said sample; and comparing an integral of said nuclear magnetic resonance peak associated with said CH proton of chloral hydrate with an integral of a nuclear magnetic resonance peak associated with at least one proton of said at least one organic solvent. In certain preferred embodiments, the organic solvent is toluene. In certain preferred embodiments, the method further comprises calculating a concentration of chloral hydrate in said dichloroacetic acid based upon said comparison of integrals of nuclear magnetic resonance peaks. In certain preferred embodiments, the calculated concentration of chloral hydrate is less than 15 ppm. In certain preferred embodiments, the calculated concentration of chloral hydrate is less than 10 ppm. In certain preferred embodiments, the calculated concentration of chloral hydrate is less than 1 ppm. In certain preferred embodiments, the dichloroacetic acid is used as a deprotecting agent in an oligonucleotide synthesis to prepare an oligonucleotide having the formula:

d(TpCpCpGpTpCpApTpCpGpCpT-pCpCpTpCpApGpGpGp) [SEQ ID NO: 1]; wherein P=P(O)S$^-$Na$^+$.

In another embodiment, the present invention provides an analytical method comprising determining whether or not a nuclear magnetic resonance spectrum taken from a sample of dichloroacetic acid includes a nuclear magnetic resonance peak associated with a CH proton of chloral hydrate, further comprising contacting an oligonucleotide that bears at least one protecting group with said dichloroacetic acid. In certain embodiments, contacting effects removal of said at least one protecting group from said oligonucleotide. In certain embodiments, said oligonucleotide from which said protecting group has been removed does not include a group having formula 5'-O—CH(OH)(CCl$_3$). In certain embodiments, said oligonucleotide from which said protecting group has been removed does not include a group having formula 5'-O—CH(CCl$_3$)—O—.

These, as well as other objects, are a result of the inventors' discovery that chloral hydrate is a common contaminant in commercially prepared dichloroacetic acid. As used herein, the term "chloral hydrate" is intended to mean a chemical compound having the structure:

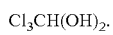

As used herein, the term "dichloroacetic acid" (DCA) is intended to mean a chemical compound having the structure:

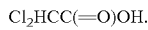

It is well-known that dichloroacetic acid (DCA) is a commonly used reagent for deblocking nucleotides during oligonucleotide synthesis. Particularly, oligonucleotide syntheses involve the repeated use of dichloroacetic acid as a deprotecting reagent for deblocking 5'-hydroxy protecting groups (Prot) (Scheme 1):

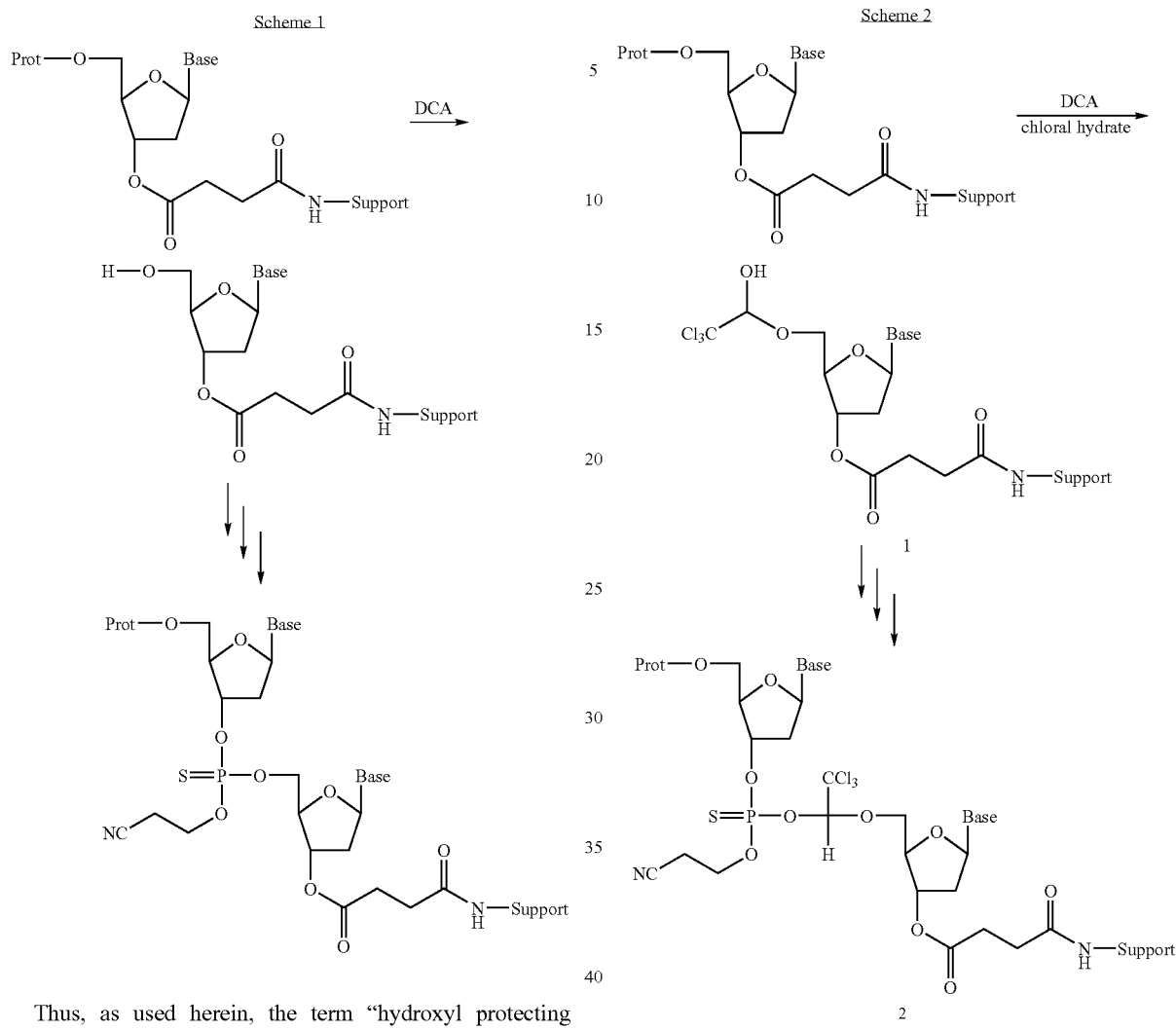

Thus, as used herein, the term "hydroxyl protecting group" (Prot) is intended to mean a chemical group that is stable under certain conditions but can be removed under other conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* (1992), 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups include dimethoxytrityl (DMT), monomethoxytrityl, 9-phenylxanthen-9-yl (Pixyl) and 9-(p-methoxyphenyl)xanthen-9-yl (Mox).

Because of the repetitious use of DCA for the removal of the oligonucleotide protecting groups, it is critical that DCA be free of contaminants which may propagate impurities and produce improper sequences of the target oligonucleotide. The inventors have discovered that the specific impurity chloral hydrate, when present in dichloroacetic acid, reacts to yield side-products, referred to herein as trichloroethanol adducts 1 and 2, shown below (Scheme 2).

The trichloroethanol adducts are extremely difficult to remove once formed and, if unchecked, propagate through each synthetic step. The inventors have discovered that varying degrees of chloral hydrate may be present in dichloroacetic acid depending upon the manufacturing process used in its preparation. Thus, a method for detecting the presence and concentration of chloral hydrate prior to its use in oligonucleotide synthesis is desirable. Specifications may then be established for the maximum concentrations of chloral hydrate tolerable in an oligonucleotide manufacturing process. In certain embodiments, the concentration of chloral hydrate tolerated is less than 15 ppm, preferably less than 10 ppm, more preferably less than 1 ppm. Most preferably, the concentration of chloral hydrate is below the limit of detection.

Accordingly, the present invention is directed, in part, to a method for testing dichloroacetic acid for the presence of chloral hydrate. The method preferably comprises taking a nuclear magnetic resonance (NMR) spectrum of a sample of the dichloroacetic acid prior to its use in a manufacturing process. Preferably, the sample contains a predetermined concentration of an internal standard. As used herein, the term "internal standard" or "standard" is intended to mean any compound, preferably a solvent, containing protons, the nuclear magnetic resonance peak of which may be compared to that of the CH proton of chloral hydrate to determine the concentration of chloral hydrate present. It is therefore preferable that the protons of the internal standard resonate at a location that is different, preferably, upfield or downfield, from chloral hydrate. Thus, it will be appreciated that in one aspect the present invention contemplates using the integral of the peak associated with the CH proton of dichloroacetic acid itself as the internal standard. If the internal standard is other than dichloroacetic acid, the internal standard is preferably selected from suitable liquid solvents. Such liquid solvents include, but are not limited to, halogenated solvents, hydrocarbon solvents, ether solvents, protic or aprotic solvents.

Suitable halogenated solvents include, but are not limited to bromodichloromethane, dibromochloromethane, bromoform, chloroform, bromochloromethane, dibromomethane, butyl chloride, dichloromethane, trichloroethylene, 1,1,1-trichloroethane, 1,1,2-trichloroethane, 1,1-dichloroethane, 2-chloropropane, 1,2,4-trichlorobenzene, o-dichlorobenzene, chlorobenzene, fluorobenzene, dichlorofluoromethane, chlorodifluoromethane, and trifluoromethane.

Suitable hydrocarbon solvents include, but are not limited to acetonitrile, benzene, cyclohexane, pentane, hexane, toluene, cycloheptane, methylcyclohexane, heptane, ethylbenzene, m-, o-, or p-xylene, octane, indane, and nonane.

Suitable ether solvents include, but are not limited to dimethoxymethane, tetrahydrofuran, 1,3-dioxane, 1,4-dioxane, furan, diethyl ether, ethylene glycol, dimethyl ether, ethylene glycol diethyl ether, diethylene glycol dimethyl ether, diethylene glycol diethyl ether, triethylene glycol diisopropyl ether, anisole, or t-butyl methyl ether.

Suitable polar protic solvents include, but are not limited to methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol 2-ethoxyethanol, diethylene glycol, 1-, 2-, or 3-pentanol, neo-pentyl alcohol, t-pentyl alcohol, cyclohexanol, benzyl alcohol, phenol, and glycerol.

Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, hexamethylphosphoramide.

In preferred embodiments, the internal standard will be stable toward acid. The internal standard is also preferably a solvent which is relatively non-volatile, thus minimizing the possibility of concentration change during standard preparation or NMR acquisition. In other preferred embodiments, the internal standard is an aprotic solvent. In other preferred embodiments, the internal standard has a relatively simple NMR spectrum, preferably, less than 4 signals. In particularly preferred embodiments, the solvent is toluene.

By way of general guidance, a known volume of dichloroacetic acid (DCA) may be dissolved in a known volume of deuterated NMR solvent. If an additional compound is used as an internal standard, i.e., one that is added to the NMR tube for the purpose of comparing the integral of the standard to that of chloral hydrate, it may be added in an concentration of, for example, approximately 40 ppm. $^1$H NMR may then be collected using any NMR spectrometer capable of providing conditions suitable for acquiring a resonance signal for each component. A ratio of chloral hydrate to dichloroacetic acid is preferably obtained by comparing the integral (the area) of the CH proton on chloral hydrate with that of the internal standard. As will be readily understood by the skilled artisan, the concentration of chloral hydrate in dichloroacetic acid may then be calculated using the ratio obtained via integral comparison, the concentration of the dichloroacetic acid and the concentration of any additional internal standard used. The dichloroacetic acid may then used accordingly.

Once the purity of dichloroacetic acid is determined by the methods described herein, it may subsequently be used for virtually any purpose. Particularly, the dichloroacetic acid may be used in an oligonucleotide synthesis to produce an oligonucleotide.

As used herein, "oligonucleotide" refers to compounds containing a plurality of monomeric subunits that are joined by phosphorus-containing linkages, such as phosphite, phosphodiester, phosphorothioate, and/or phosphorodithioate linkages. The monomeric subunits may contain both naturally occurring (i.e. "natural") and non-naturally occurring synthetic moieties, for example, nucleosidic subunits containing modified sugar and/or nucleobase portions. Thus, the term oligonucleotide includes oligonucleotides, their analogs, and synthetic oligonucleotides. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

In certain preferred embodiments, the oligonucleotide prepared using dichloroacetic acid as a deprotecting agent that has been tested according to the methods of the present invention has the formula:

d(TpCpCpGpTpCpApTpCpGpCpT-pCpCpTpCpApGpGpGp) [SEQ ID NO: 1]; wherein P=P(O)S$^-$Na$^+$.

As used herein "oligonucleotide synthesis" is intended to have its art-recognized meaning whereby an oligonucleotide is prepared using synthetic methods well known to the ordinarily skilled artisan. By way of general guidance, the 3'-most nucleoside may be anchored to a solid support which is functionalized with hydroxyl or amino residues. The additional nucleosides may be subsequently added in a step-wise fashion to form the desired linkages between the 3'-functional group of the incoming nucleoside, and the 5'-hydroxyl group of the support bound nucleoside. In any case, the chosen oligonucleotide synthesis preferably uses a protecting group to render certain groups unreactive, for example, the 5'-hydroxy group of the incoming nucleoside. Following coupling, the 5'-hydroxy protecting group may then be removed by the addition of dichloroacetic acid which has been tested for chloral hydrate content.

The present invention is also directed to producing oligonucleotides that are free of side products caused by the use of dichloroacetic acid contaminated with chloral hydrate. One such side product is a trichloroethanol adduct which is the result of chloral hydrate's reaction with the 5'-hydroxy group (Scheme 2). Thus, as used herein, the term "trichloroethanol adduct" is intended to mean a nucleoside wherein the 5'-hydroxy has reacted with chloral hydrate to produce an impurity having the moeity: $HOCH(CCl_3)$—O—$CH_2$—* wherein * indicates the attachment point to the 5' position of a nucleoside. It will be appreciated that following reaction with an incoming nucleoside to form an oligonucleotide, the ethanol adduct will have the structure P—O—$CH(CCl_3)$—O—$CH_2$* in an oligonucleotide, wherein P is the phosphorus atom of the incoming nucleoside.

In certain embodiments, the present invention provides a method for producing an oligonucleotide free of trichloroethanol adduct. Generally, the method comprises testing dichloroacetic acid for the presence of chloral hydrate prior to use as a deprotecting reagent. If chloral hydrate is present, the concentration can be determined by taking and NMR and comparing the integral of the nuclear magnetic resonance peak of the CH proton of chloral hydrate with the integral of the nuclear magnetic resonance peak of protons of an internal standard to determine the concentration of chloral hydrate present in the dichloroacetic acid, and using the dichloroacetic acid if the concentration of chloral hydrate is below an acceptable threshold concentration. In certain embodiments, the acceptable concentration of chloral hydrate in the dichloroacetic acid is less than 15 ppm, preferably less than 10 ppm, more preferably 5 ppm, and even more preferably less than 1 ppm. Most preferably, the concentration of chloral hydrate is below the level of detection.

The oligonucleotides of the present invention may be synthesized through the use of a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. No. Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23, hereby incorporated by reference in its entirety.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* (1991), 19, 1527, hereby incorporated by reference in its entirety), TentaGel Support—an aminopolyethyleneglycol derivatized support (see, e.g., Wright, et al., *Tetrahedron Letters* (1993), 34, 3373, hereby incorporated by reference in its entirety) and Poros—a copolymer of polystyrene/divinylbenzene.

Following reaction with an incoming nucleoside, the phosphorus atom may be sulfurized. Sulfurizing agents used during oxidation to form phosphorothioate and phosphorodithioate linkages include Beaucage reagent (see e.g. Iyer, R. P., et. al., *J. Chem. Soc.* (1990) 112, 1253–1254, and Iyer, R. P., et. al., *J. Org. Chem.* (1990) 55, 4693–4699); tetraethylthiuram disulfide (see e.g., Vu, H., Hirschbein, B. L., *Tetrahedron Lett.* (1991) 32, 3005–3008); dibenzoyl tetrasulfide (see e.g., Rao, M. V., et. al, *Tetrahedron Lett.* (1992), 33, 4839–4842); di(phenylacetyl)disulfide (see e.g., Kamer, P. C. J., *Tetrahedron Lett.*, 1989, 30, 6757–6760); Bis(O,O-diisopropoxy phosphinothioyl)disulfids (see Stec et al., *Tetrahedron Lett.*, 1993, 34, 5317–5320); 3-ethoxy-1,2,4-dithiazoline-5-one (see *Nucleic Acids Research*, 1996 24, 1602–1607, and *Nucleic Acids Research* (1996) 24, 3643–3644); Bis(p-chlorobenzenesulfonyl)disulfide (see *Nucleic Acids Research* (1995) 23, 4029–4033); sulfur, sulfur in combination with ligands like triaryl, trialkyl, triaralkyl, or trialkaryl phosphines. The foregoing references are hereby incorporated by reference in their entirety.

Other useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs prepared by using dichloroacetic acid tested according to the present invention may be hybridizable to a specific target and preferably comprise from about 5 to about 50 monomer subunits. It is more preferred that such compounds comprise from about 10 to about 30 monomer subunits, with 15 to 25 monomer subunits being particularly preferred. When used as building blocks in assembling larger oligomeric compounds, smaller oligomeric compounds are preferred. Libraries of dimeric, trimeric, or higher order compounds can be prepared for use as synthons in the methods of the invention. The use of small sequences synthesized via solution phase chemistries in automated synthesis of larger oligonucleotides enhances the coupling efficiency and the purity of the final oligonucloetides. See, for example: Miura, K., et al., *Chem. Pharm. Bull.* (1987), 35, 833–836; Kumar, G., and Poonian, M. S., *J. Org. Chem.* (1984) 49, 4905–4912; Bannwarth, W., *Helvetica Chimica Acta*, (1985) 68, 1907–1913; Wolter, A., et al., *nucleosides and nucleotides*, 1986, 5, 65–77, each of which are hereby incorporated by reference in their entirety.

It will be recognized that the oligonucleotides prepared using dichloroacetic acid of the invention can be used in diagnostics, therapeutics and as research reagents and kits. They can be used in pharmaceutical compositions by including a suitable pharmaceutically acceptable diluent or carrier. The present invention may be further understood by reference to the following examples.

EXAMPLE 1

Detection of Chloral Hydrate in Dichloroacetic Acid

A test sample of dichloroacetic acid (DCA, 0.15 mL) was dissolved in deuterated acetonitrile (0.5 mL) containing 40 ppm of toluene. $^1H$ NMR spectra were collected using a Varian Unity 400 NMR spectrometer under the following conditions: 30 degree pulse, sweep width of 6997.9 Hz, 32 k complex points and a 45 second total recycle delay. Approximately 1000 transients were run for each sample. The data was processed by zero filling to 64 k complex points with an exponential line-broadening of 0.3 Hz. The first two points were reproduced through linear prediction to smooth base-line and further smoothed after FFT by spline fit.

The concentration of chloral hydrate was measured by comparing the integral of the peak associate with the CH proton on chloral hydrate with that of the $CH_3$ group of toluene. Dichloroacetic acid was then used to prepare the 20 mer according to the procedure set forth in Example 2.

EXAMPLE 2

Preparation of (d(TpCpCpGpTpCpApTpCpGpCpTpCpCpTpCpApGpGpGp) [SEQ ID NO: 1]; wherein P=P(O)S⁻Na⁺.

5'-O-DMT-N²-isobutyryl-2'-deoxyguanosine derivatized Primer HL 30 support was packed into a steel reactor vessel.

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: P(O)S-Na+ linkage

<400> SEQUENCE: 1
tccgtcatcg ctcctcaggg                                              20
```

A solution of dichloroacetic acid in toluene (10%, v/v) was added to deprotect the protected hydroxy group and the product was washed with acetonitrile. A solution of 5'-O-DMT-N²-isobutyryl-2'-deoxyguanosine-3'-O-(2-cyanoethyl)-N,N-diisopropylphosphoramidite (0.2 M) and a solution of 1-H-tetrazole in acetonitrile (0.45 M) were added and allowed to react for 5 minutes at room temperature. A solution of phenylacetyl disulfide in 3-picoline-acetonitrile (0.2 M, 1:1, v/v) was added and allowed to react at room temperature for 2 minutes. The product was washed with acetonitrile (1:4 v/v) and N-methylimidazole-pyridine-acetonitrile (2:3:5, v/v/v). After 2 minutes the capping mixture was removed by washing the product with acetonitrile.

A solution of dichloroacetic acid in toluene (3% v/v) was added to deprotect the 5'-hydroxy group and the product was washed with acetonitrile. A solution of 5'-O-DMT-N²-isobutyryl-2'-deoxyguanosine-3'-O-(2-cyanoethyl)-N,N-diisopropylphosphoramidite (0.2 M) and a solution of 1-H-tetrazole in acetonitrile (0.45 M) were added and allowed to react for 5 minutes at room temperature. A solution of phenylacetyl disulfide in 3-picoline acetonitrile (0.2 M, 1:1, v/v) was added and allowed to react at room temperature for 2 minutes. The product was washed with acetonitrile followed by a capping mixture (1:1, v/v) of acetic anhydride acetonitrile (1:4, v/v) and N-methylimidazole-pyridine-acetonitrile (2:3:5, v/v/v). After 2 minutes the capping mixture was removed by washing the product with acetonitrile.

The process of deprotecting the 5'-hydroxyl group, adding a phosphoramidite and an activating agent, sufurizing and capping with intervening wash cycles was repeated 17 additional cycles to prepare the 20 mer. The resulting support bound oligonucleotide was treated with aqueous ammonium hydroxide (30%) for 12 hours at 60° C. and the products were filtered. The filtrate was concentrated under reduced pressure and a solution of the residue in water was purified by reversed phase high performance liquid chromatography. The appropriate fractions were collected, combined, and concentrated in vacuo. A solution of the residue in water was treated with aqueous sodium acetate solution (pH 3.5) for 45 minutes. The title 2'-deoxyphosphorothioate 20 mer oligonucleotide was collected after precipitation by addition of ethanol.

As those skilled in the art will appreciate, numerous changes and modifications may be made to the preferred embodiments of the invention without departing from the spirit of the invention. It is intended that all such variations fall within the scope of the invention.

What is claimed is:

1. A method of preparing an oligonucleotide, comprising:
   providing a support-bound nucleotide comprising a 5'-hydroxyl group;
   coupling an additional nucleoside to said support-bound nucleoside, said additional nucleoside comprising a 5'-hydroxy protecting group and a 3'-functional group capable of linking to said 5'-hydroxyl group;
   selecting dichloroacetic acid having a chloral hydrate concentration of less than 15ppm; and
   removing said 5'-hydroxy protecting group in the presence of said dichloroacetic acid.

2. The method of claim 1, wherein said dichloroacetic acid has a chloral hydrate concentration of less than 10 ppm.

3. The method of claim 1, wherein said dichloroacetic acid has a chloral hydrate concentration of less than 5 ppm.

4. The method of claim 1, wherein said dichloroacetic has a chloral hydrate concentration of less than 1 ppm.

5. The method of claim 1, further comprising taking a nuclear magnetic resonance spectrum of said dichloroacetic acid and integrating a nuclear magnetic resonance peak associated with a CH proton of chloral hydrate.

6. A method of removing a 5'-hydroxyl protecting group during an oligonucleotide synthesis, comprising: selecting dichloroacetic acid having a chloral hydrate concentration of less than 15 ppm; and
   contacting a 5'-hydroxyl protecting group of an oligonucleotide with said dichloroacetic acid.

7. The method of claim 6, further comprising determining whether a nuclear magnetic resonance spectrum of said dichloroacetic acid includes a nuclear magnetic resonance peak associated with a CH proton of chloral hydrate.

8. A method comprising:
   testing dichloroacetic acid for the presence of chloral hydrate;

determining the chloral hydrate concentration in said dichloroacetic acid is less than 15 ppm; and contacting a 5'-hydroxy protecting group of an oligonucleotide with said dichloroacetic acid under conditions effective to remove said protecting group.

9. The method of claim 8, further comprising coupling a nucleoside to said 5'-hydroxy protecting group, said nucleoside comprising a 3'-functional group capable of linking to said 5'-hydroxyl group.

* * * * *

UNITED STATES PATENT AND TRADEMARK OFFICE
CERTIFICATE OF CORRECTION

PATENT NO. : 7,173,123 B2  Page 1 of 1
APPLICATION NO. : 10/679805
DATED : February 6, 2007
INVENTOR(S) : Patrick Wheeler and Daniel C. Capaldi It is certified that error appears in the above-identified patent and that said Letters Patent is hereby corrected as shown below:

Column 12, Claim 1, line 36, please delete "nucleoside, said additional nucleoside" and insert therefor --nucleotide, said additional nucleotide--;

Column 14, Claim 9, line 3, please delete "nucleoside" and insert therefor --nucleotide--.

Signed and Sealed this

Tenth Day of April, 2007

JON W. DUDAS
*Director of the United States Patent and Trademark Office*